United States Patent [19]

Sherlock

[11] Patent Number: 5,800,501
[45] Date of Patent: Sep. 1, 1998

[54] INTRAVAGINAL OR INTRARECTAL ELECTRODE

[76] Inventor: Roy Sherlock, Barn Lodge, Swanton Morely, Dereham, United Kingdom

[21] Appl. No.: 669,295

[22] PCT Filed: Dec. 22, 1994

[86] PCT No.: PCT/GB94/02808

§ 371 Date: Jun. 24, 1996

§ 102(e) Date: Jun. 24, 1996

[87] PCT Pub. No.: WO95/17922

PCT Pub. Date: Jul. 6, 1995

[30] Foreign Application Priority Data

Dec. 24, 1993 [GB] United Kingdom ............... 9326422
Oct. 12, 1994 [GB] United Kingdom ............... 9420541

[51] Int. Cl.$^6$ ............................................. A61N 1/00
[52] U.S. Cl. .................. 607/138; 607/116; 600/373
[58] Field of Search ...................... 607/138, 116; 600/184, 220; 128/639, 642, 733

[56] References Cited

U.S. PATENT DOCUMENTS

| 659,409 | 10/1900 | Mosher | 607/138 |
|---|---|---|---|
| 4,881,526 | 11/1989 | Johnson et al. | 607/138 |
| 5,046,511 | 9/1991 | Maurer et al. | 607/138 |

FOREIGN PATENT DOCUMENTS

| 8807820 | 9/1988 | Germany. | |
| 584844 | 12/1977 | U.S.S.R. | 607/138 |
| 2284991 | 6/1995 | United Kingdom. | |

OTHER PUBLICATIONS

B.V. Enraf-Nonius Delft—Advertisement/Trade publication entitled: "The Hygienic Solution for Incontinence", date unknown.

EuroSurgical Limited—Advertisement/Trade Publication entitled: "INNOVA Feminine Incontinence Treatment System Design Rationale", date unknown.

*Primary Examiner*—John P. Lacyk
*Assistant Examiner*—David M. Ruddy
*Attorney, Agent, or Firm*—Galgano & Burke

[57] ABSTRACT

An intravaginal or intrarectal electrode for electrostimulation and/or biofeedback monitoring of muscle activity, which electrode comprises a pair of electrode lines each comprising a lead 10, 11 with an electrode terminus 7, 7' and a probe body 1 having an enlarged head portion 2 to seat within the vagina or rectum or the rectum and having at least one longitudinal convex surface 5, 7 extending for a majority of the length of the probe body 1 head portion and carrying at least one of the electrode termini, a narrower neck portion 3 adapted to seat at the introitus of the vagina or of the rectum and handle means 4 extending from the neck portion 3 to enable the probe body 1 head and neck to be inserted into and withdrawn from the vagina or the rectum.

16 Claims, 4 Drawing Sheets

INTRAVAGINAL OR INTRARECTAL ELECTRODE

FIELD OF THE INVENTION

The present invention relates to an intravaginal or intrarectal electrode for electro-stimulation and/or bio-feedback monitoring of the pubo-visceral musculature and most especially the pelvic floor primarily as a treatment for various pelvic floor dysfunctions including urinary stress incontinence.

BACKGROUND TO THE INVENTION

Electro stimulation of the pelvic floor muscle is a technique that has been used for many years now to treat urinary incontinence, where the patients have weak or inactive muscles closing the urethra whereby control of voiding of the contents of the bladder is lost. Electro-stimulation has been found to be effective in increasing muscle strength and the bio-feedback monitoring of muscular activity is valuable in assessment and re-education of the patient for correct pelvic floor contraction.

For the purposes of electro stimulation and bio feedback monitoring an extensive range of intravaginal and intrarectal electrode probes exist.

Both of these techniques require an intra-vaginal or intra-rectal electrode. Stimulation requires an electrode that will deliver an appropriate stimulus to the pelvic floor musculature at a depth of approximately 3.5 to 5 cms from the introitus (entrance to the vagina) and similarly, a bio-feedback electrode will be required to pick up the natural electrical activity of the muscle for display on a bio-feedback monitor.

Both techniques require a sound interface between the electrode and the muscle. A sufficient surface area of the conductive part of the electrode is required to allow safe and comfortable stimulation and, in bio-feedback, the conductive area must be so shaped and positioned to provide a sound and interference-free signal to be monitored.

Seemingly without exception, however, these conventional electrode probes are of a geometry whereby they are not firmly held within the vagina or rectum when inserted and are susceptible to expulsion by the muscular contraction. Inevitably, therefore, these conventional electrode probes are largely limited to use in a clinical environment where they are held in place and generally require the patient to be recumbent during their use. They are largely unsuited for ambulatory use whereby the patient can remain mobile and are especially troublesome for the many patients who are young mothers who do not have the time or opportunity to sit or lie down for sessions which frequently last for half an hour at intervals several times daily. Furthermore, in some treatment protocols it is necessary for low level stimulation to be applied for several hours at a time. It will be appreciated, therefore that the existing electrodes for pubo-visceral muscle stimulation are subject to an extremely inconvenient drawback.

It is a general objective of the present invention to overcome the above problem to provide an intravaginal or intrarectal electrode suitable for ambulatory use and to improve the interfacing between the electrode and the muscle for increased operational efficiency.

SUMMARY OF THE INVENTION

According to a first aspect of the present invention there is provided an intravaginal or intrarectal electrode for electro-stimulation and/or bio feedback monitoring of muscle activity, which electrode comprises:

a pair of electrode lines each comprising a lead with an electrode terminus; and a probe body having an enlarged head portion to seat within the vagina or the rectum and carrying at least one of the electrode terrini and having at least one longitudinal concave surface extending for a majority of the length of the probe body head portion, a narrower neck portion adapted to seat at the introitus of the vagina or of the rectum, and handle means extending from the neck portion to enable the probe body head and neck to be inserted into and withdrawn from the vagina or the rectum. Preferably the concave surface is a recess, cavity or void into which the muscle tissue may extend in use.

Advantageously either the neckward end of the probe body head portion or the apex, end remote from the neck, of the probe body head portion is provided with a gap whereby the opposing side wall lengths of the probe body head portion may be compressed together during muscle contraction and the wall lengths are resilient enabling them to return to their original position upon muscle relaxation.

Suitably each electrode terminus is mounted in an electro conductive pad which is integrally mounted to the probe body head portion or demountably mounted thereto.

Preferably the probe body head portion has a substantially flattened longitudinal aspect whereby rotation of the probe body head portion about its longitudinal axis is restricted.

According to a second aspect of the present invention there is provided an intravaginal or intrarectal electrode for pelvic floor muscle electro stimulation and/or bio feedback monitoring, which is substantially as hereinafter described with reference to any suitable combination of the accompanying drawings.

According to a third aspect of the present invention there is provided an intravaginal or intrarectal electrode probe body having an enlarged head portion to seat within the vagina or rectum and having at least one longitudinal convex surface extending for a majority of the length of the probe body head portion and carrying at least one electrode terminus, a narrower neck portion adapted to seat at the introitus of the vagina or rectum and handle means extending from the neck portion to enable the probe body head and neck to be inserted into and withdrawn from the vagina or rectum.

BRIEF DESCRIPTION OF THE DRAWINGS

Preferred embodiments of the present invention will now be more particularly described, by way of example, with reference to the accompanying drawings, wherein:

FIG. 18 is a plan view of the probe from above and FIGS. 19 and 20 are side elevation and front elevation views of the probe.

DESCRIPTION OF THE PREFERRED EMBODIMENTS

Figure 1:
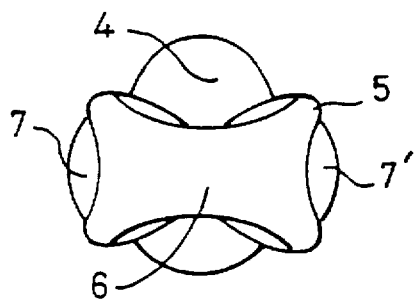
FIGS. 1 to 4 are, respectively, a top plan view, a bottom plan view, a side elevation and a front elevation of an electrode probe body of the first embodiment of the invention.
Figure 2:
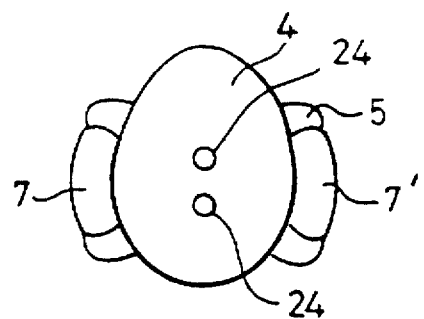
Figure 3:
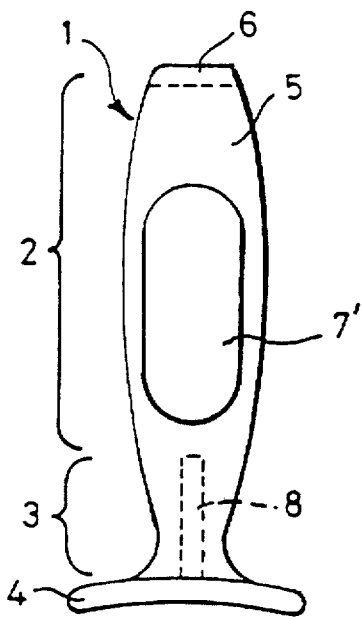

Referring to the first preferred embodiment, illustrated in FIGS. 1 to 5, the electrode probe body 1 illustrated comprises an elongate head portion 2 shaped as a loop and adapted to seat within the vaginal atrium, a narrower neck portion 3 adapted to seat at the introitus to the vagina allowing the superficial part of the pubo-coccyged muscle to constrict thereabout, and a flange 4 extending from the neck 3 to serve as a handle and as a rebate to prevent drawing of the probe fully into the vagina.

The typical length of the probe body head portion 2 is 75 mm with the broadest part of the probe body head portion being approximately 37 mm across.

For rectal use the typical length would be approximately 50 mm and the typical broadest width being about 20 mm.

Figure 4:
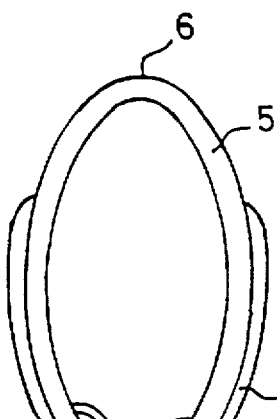
Figure 5:
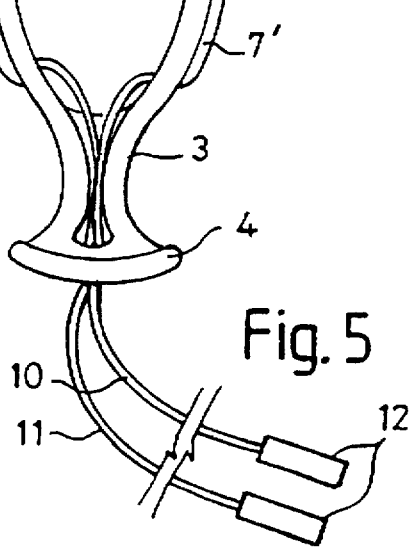
FIG. 5 is a front elevation similar to that of FIG. 4 but showing the electrode lines in place.
Figure 6:
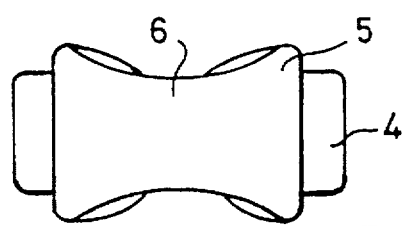
FIGS. 6 to 10 are, respectively, a top plan view, a side elevation view, a front elevation view, a longitudinal sectional view taken along the line IX—LX in FIG. 8, and a longitudinal sectional view taken along the line X—X in FIG. 7 of a second embodiment of electrode probe body.
Figure 7:
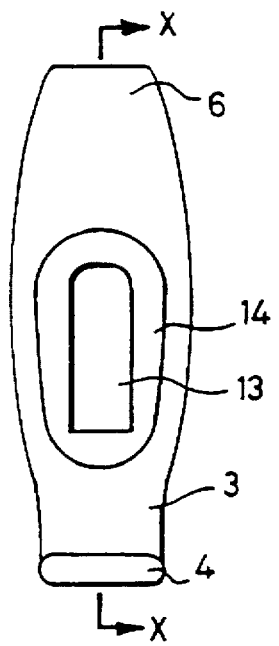
Figure 8:
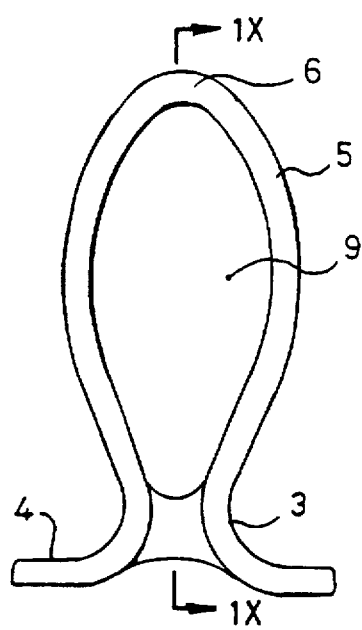
Figure 9:
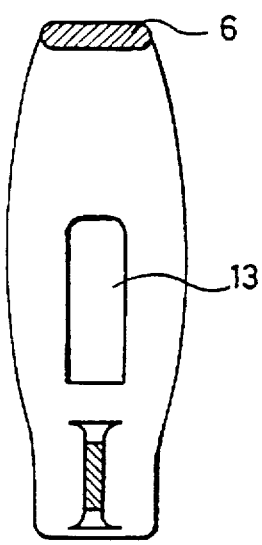
Figure 10:
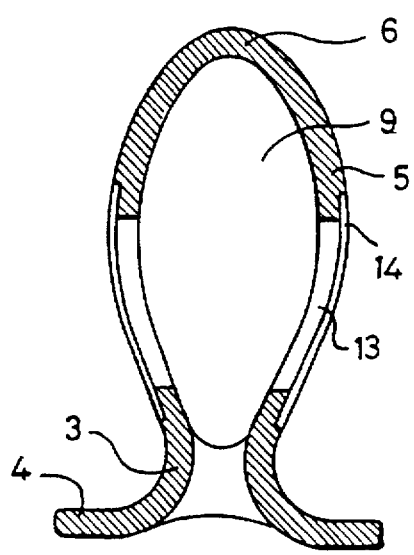

As will be appreciated from FIGS. 4 and 5, the probe body head portion 2 is broadly elliptical and, furthermore, broadly ovoid in front elevation having a broader neckward end than apex 6. In the illustrated embodiment the broadening is attributable to bulging electro-conductive electrode terminal pads 7, 7' which suitably have a surface area of approximately 35×15 mm. The purpose of this basal broadening is not only to provide an additional physical barrier to expulsion inward of the narrower neck 3 but by provision of a predominance of electro active surface of the electrode terminal pads 7, 7' facing toward neck 3 of the probe body 1 the resultant force acting upon the probe body during muscular contraction will tend to be inwardly into the vagina.

As illustrated, the electrode terminal pads 7, 7' are integrally formed on the lower two thirds of the lateral walls 5 of the probe body head portion 2.

The probe body is suitably formed of an injection moulded plastics material such as, for example, medical grade acrylic and the electrode terminal pads are suitably of a flexible carbon impregnated conductive polymer which may be silicone polymer and which is also injected moulded. The probe body 1 other than the electro active parts of the electrode pads 7, 7' is electrically non conductive.

As a further aid to increasing the inwardly acting resultant force upon muscular contraction, the bulging terminal pads 7, 7' are preferably arranged to be predominantly positioned at their neckward end of the head portion 2.

The electrical supply to the terminal pad 7, 7' is provided via electrode lines 10, 11 each extending to a respective pad 7, 7' and having a corresponding plug 12 at its remote end for fitment to a stimulator device and/or bio feedback device. For optimum convenience the device to which the probe is fitted is suitably a portable personal device.

The electrode lines 10, 11 are insulated wires, approximately 15 cms in length connected via stainless steel pins into the conductive polymer pads 7, 7' and terminate at their distal ends in the insulated 2 mm dia. female connector plugs 12 to allow connection to the stimulation or bio-feedback equipment. These wires may be gripped in two strain-relief, 'wire-management' channels moulded into the probe body at bridging web 8 and exit the probe via a hole or holes 24 in the flange 4.

It will be appreciated from the drawings that the probe body head portion 2 illustrated has effectively two longitudinal convex surfaces, as viewed in longitudinal section of the probe body 1, extending for a majority of the length of the probe body head portion 2 and these are suitably arranged to slightly pre-tension the pelvic floor muscle, improving the surface area for electrical contact and optimising responsiveness as well as improving the security of location of the probe within the vagina both longitudinally and, due to absence of front and rear walls, in radial orientation.

Figure 18:
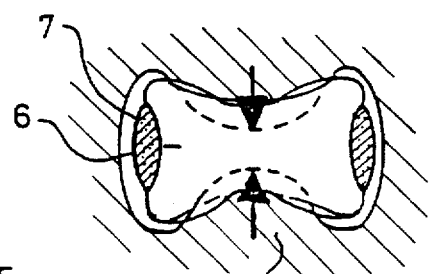
Figure 19:
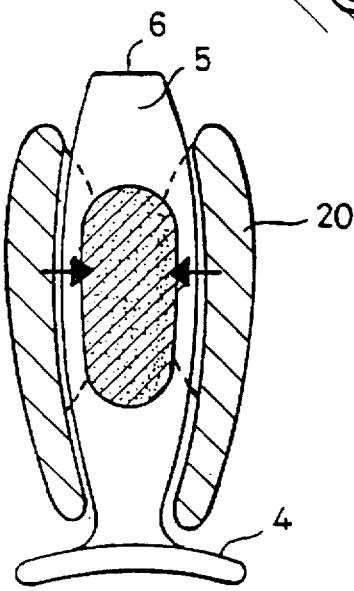
Figure 20:
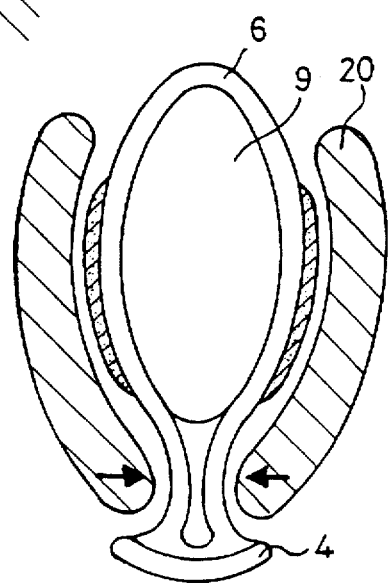

Being formed as a loop, the probe head portion 2 has a void 9 in the plane transverse to the bulging side walls 5 into which the pelvic floor muscle 20 may extend in use as may be best appreciated from FIGS. 18 and 19.

The pelvic floor muscle 20 enfolds into the void 9 from front and rear and presses from the sides against the side walls 5 and the electrode terminal pads 7, 7'.

The relatively flat front to rear dimension of the probe body head portion 2 in contrast to its broad lateral dimensions and the presence of the void 9 in contrast to the broadening provided by the pads 7 all assist in maintaining the radial orientation of the probe within the vagina. Since the preferred orientation for effective muscle stimulation and comfort is with the electrodes arranged on an East/West axis, ie to left and right of the patients' body, this configuration restricting the change in orientation serves an important role.

Figure 17:
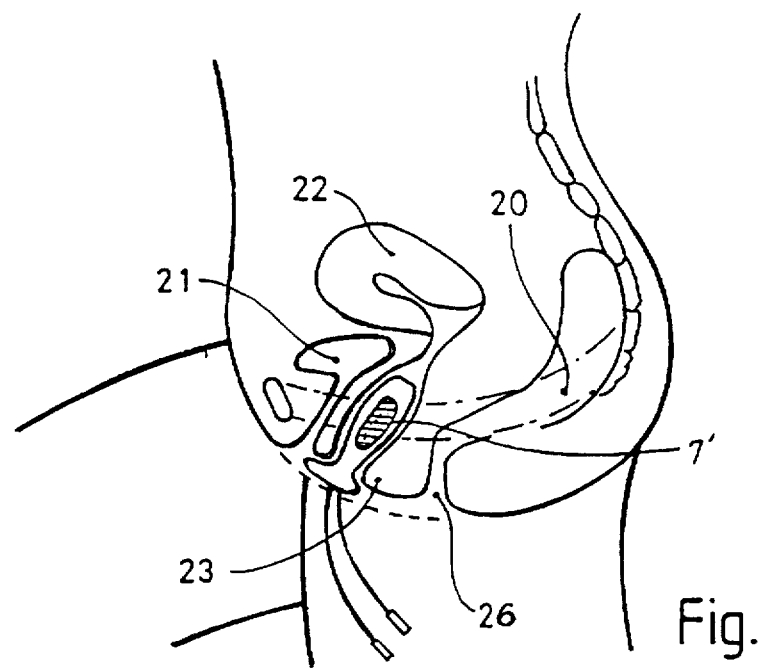
FIGS. 17 to 20 are views of the first embodiment of electrode probe in use and comprising, respectively, a schematic longitudinal sectional view of the lumbar region of a patient with probe in place.

For ease of reference when referring to FIG. 17, the introitus to the vagina is illustrated at 23, the rectum at 26 the bladder at 21 and the uterus at 22. It will be seen that the pelvic floor muscle extends from the pubis to the coccyx at the base of the spine passing around the urethra, the vagina and the rectum.

Turning now to the embodiment of FIGS. 6 to 10, as with the first embodiment this comprises a looped head portion 2 but differs from the first embodiment in that the electrode terminal pads 7, 7' are not integrally formed on the probe body head portion 2 but are detachably mounted thereto and fit into sockets 13 which have rebated rims 14. This design allows for ease of cleaning.

Figure 11:
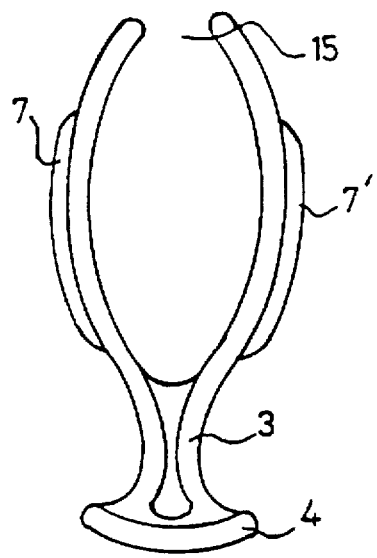
FIGS. 11 and 12 are, respectively, front elevation views of third and fourth embodiments of electrode probe body.
Figure 12:
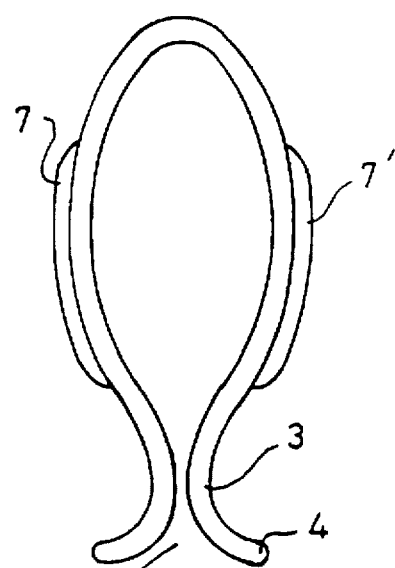
Figure 13:
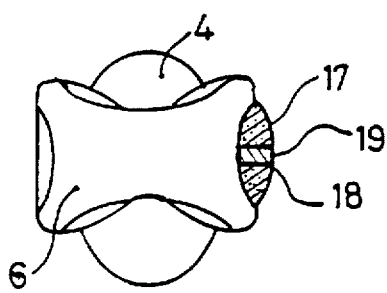
FIGS. 13 to 16 are, respectively, top plan view, bottom plan view, side elevation view and front elevation views of a fifth embodiment of electrode probe body.

Turning to the embodiments of FIGS. 11 and 12, these are two variants which are adapted to enable greater dynamic contraction of the muscles by allowing the flexing of the side walls 5 of the probe body head portion 2.

Each of these third and fourth embodiments has a gap 15, 16 respectively enabling the opposing side walls 5 to be pressed together during muscle contraction while the resilience of the probe body restores the side walls 5 to their original position upon relaxation of the muscles. By way of addition or alternative to provision of such a gap, the probe body 1 is suitably of a relatively soft flexible material such as silicone rubber.

FIGS. 13 to 16 illustrate a fifth embodiment in which both anode and cathode electrode 17, 18 are mounted to a single side wall 5 of the probe body head portion 2 separated by an insulating strip 9. This variant enables more localised stimulation.

Figure 14:
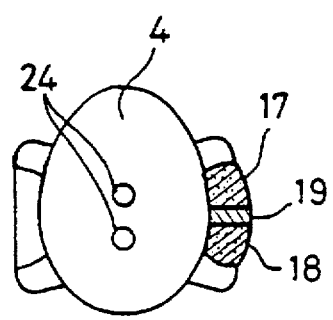
Figure 15:
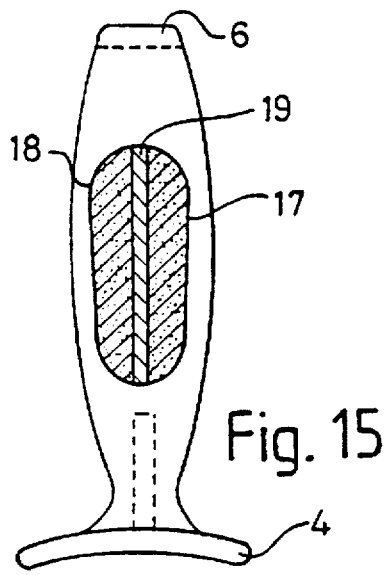
Figure 16:
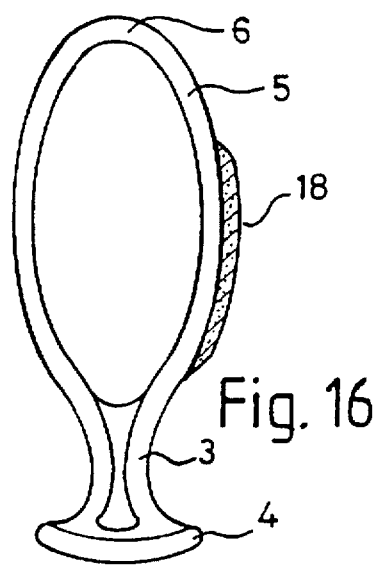

In FIG. 14 the apertures 24 for insertion of the electrode lines 10, 11 can be seen. It is not essential that both cathode and anode electrodes have their termini mounted to the probe body head portion 2. For some purposes it may be preferable to mount just one of the two electrodes to the probe body head portion 2 and to apply the other electrode terminus independently such as, for example, by a skin mounted plate.

I claim:

1. An intravaginal or intrarectal electrode for electro-stimulation and biofeedback monitoring of muscle activity, which electrode comprises:

a pair of electrode lines each comprising an electrode terminus with an electroactive surface; and a probe body having an enlarged head portion adapted to seat within an area of the vagina or the rectum and having at least one longitudinal convex external surface extending for a majority of the length of said probe body head portion and carrying at least one of the electrode termini, in use, a narrower neck portion adapted to seat at the introitus of the vagina or the rectum, and handle means extending from said neck portion to enable said probe body head and said neck to be inserted into and withdrawn from said area of the vagina or the rectum, wherein said probe head portion has at least one longitudinal concave internal surface defining a recess extending at least for a majority of the length of said probe head portion whereby upon electro-stimulation of the pelvic floor muscle by the electroactive surfaces of said electrode termini, the pelvic floor muscle contracts against the convex external surface and around the concave internal surface, the upper internal walls of said recess of said probe body in said probe body's normal attitude of operation, in use, bias said probe body against expulsion from said area of the vagina or rectum.

2. An electrode as claimed in claim 1, wherein each terminus is positional with a predominance of electroactive surface facing toward said neck of said probe body whereby the resultant force acting upon said probe, in use, upon contraction of the pelvic floor muscle acts inwardly into the vagina or rectum.

3. An electrode as claimed in claim 2, wherein said probe body head portion is substantially elliptical in elevation view.

4. An electrode as claimed in claim 3, wherein said probe body head portion is substantially ovoid in elevation view at least with each electrode terminus in place so that said probe body head portion has a broader neckward end.

5. An electrode as claimed in claim 1, wherein said head of said probe body is formed as a continuous loop as viewed in longitudinal elevation defining a cavity adapted to receive a fold of contracted pelvic floor muscle.

6. An electrode as claimed in claim 1, wherein said handle means comprises a flange which detains said electrode against being drawn further into said area of the vagina or rectum upon muscular contraction but presents a low profile to render the device unobtrusive.

7. An electrode as claimed in claim 5, wherein said probe body is formed as a discontinuous loop wherein the neckward end of said probe body head portion remote from the neck, of said probe body head portion is provided with a gap whereby the opposing side wall lengths of said probe body head portion may be compressed together during muscle contraction and are resilient enabling them to return to their original position upon muscle relaxation.

8. An electrode as claimed in claim 1, wherein each electrode terminus is mounted in an electro conductive pad which is integrally mounted to said probe body head portion.

9. An electrode as claimed in claim 1, wherein said probe body head portion has a substantially flattened longitudinal aspect whereby rotation of the probe body head portion about its longitudinal axis is restricted.

10. An electrode as claimed in claim 5, wherein said head of said probe body is formed as a discontinuous loop wherein the apex end remote from the neck, of said probe body head portion is provided with a gap whereby the opposing side wall lengths of said probe body head portion may be compressed together during muscle contraction and are resilient enabling them to return to their original position upon muscle relaxation.

11. An electrode as claimed in claim 1, wherein said head of said probe body is formed as a discontinuous loop as viewed in longitudinal elevation defining a cavity adapted to receive a fold of contracted pelvic floor muscle.

12. An electrode as claimed in claim 1, wherein each electrode terminus is mounted in an electro conductive pad which is selectively engageable with said probe body head portion.

13. An intravaginal or intrarectal electrode for electro-stimulation and biofeedback monitoring of muscle activity, which electrode comprises:

a pair of electrode lines each comprising an electrode terminus with an electroactive surface; and a probe body having an enlarged head portion to seat within an area of the vagina or the rectum and having at least one longitudinal convex external surface extending for a majority of the length of said probe body head portion and carrying at least one of the electrode termini, in use, a narrower neck portion adapted to seat at the introitus of the vagina or the rectum, and handle means extending from said neck portion to enable said probe body head and said neck to be inserted into and withdrawn from said area of the vagina or the rectum, wherein said probe head portion has a recess radially outwardly openfacing and radially angled apart from the convex surface with respect to the longitudinal axis of said probe and extending for a substantial proportion of the length of said head portion whereby upon electro stimulation of the pelvic floor muscle by the electroactive surfaces of said electrode termini, the pelvic floor muscle contracts against the convex external surface and into said recess, the end walls of which recess said probe body against expulsion from said area of the vagina or rectum; and wherein said probe body is formed as a loop as viewed in longitudinal elevation defining a cavity adapted to receive a fold of contracted pelvic floor muscle.

14. An electrode as claimed in claim 13, wherein said probe body is formed as a discontinuous loop wherein the neckward end of said probe body head portion remote from the neck, of said probe body head portion is provided with a gap whereby the opposing side wall lengths of said probe body head portion may be compressed together during muscle contraction and are resilient enabling them to return to their original position upon muscle relaxation.

15. An electrode as claimed in claim 13, wherein said head of said probe body is formed as a discontinuous loop wherein the apex end remote from the neck, of said probe body head portion is provided with a gap whereby the opposing side wall lengths of said probe body head portion may be c ompr essed together during muscle contraction and are resilient enabling them to return to their original position upon muscle relaxation.

16. An intravaginal or intrarectal electrode for electro-stimulation and bio feedback monitoring of muscle activity, which electrode comprises:

a pair of electrode lines each comprising a lead with an electrode terminus; and a probe body ha ving an enlarged head portion adapted to seat within the vagina or the rectum and carrying at least one of the electrode termini and having at least one longitudinal concave surface extending for a majority of the length of the probe body head portion, a narrower neck portion adapted to seat at the introitus of the vagina or of the rectum, and handle means extending from the neck portion to enable the probe body head and neck to be inserted into and withdrawn from the vagina or the rectum.

* * * * *